US009322712B2

(12) United States Patent
Neshat et al.

(10) Patent No.: US 9,322,712 B2
(45) Date of Patent: Apr. 26, 2016

(54) TERAHERTZ TIME-DOMAIN SPECTROSCOPIC ELLIPSOMETRY SYSTEM

(71) Applicants: Mohammad Neshat, Baltimore, MD (US); N. Peter Armitage, Baltimore, MD (US)

(72) Inventors: Mohammad Neshat, Baltimore, MD (US); N. Peter Armitage, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 213 days.

(21) Appl. No.: 13/841,316

(22) Filed: Mar. 15, 2013

(65) Prior Publication Data

US 2014/0264032 A1    Sep. 18, 2014

(51) Int. Cl.
*G01N 21/3586* (2014.01)
*G01J 3/42* (2006.01)
*G01N 21/21* (2006.01)

(52) U.S. Cl.
CPC ............... *G01J 3/42* (2013.01); *G01N 21/211* (2013.01); *G01N 21/3586* (2013.01)

(58) Field of Classification Search
USPC ....................................... 250/339.08, 339.07
See application file for complete search history.

(56) References Cited

U.S. PATENT DOCUMENTS

| 8,416,408 | B1 * | 4/2013 | Herzinger et al. | ............. 356/364 |
| 2005/0156110 | A1 * | 7/2005 | Crawely | ..................... 250/338.1 |
| 2007/0158571 | A1 * | 7/2007 | Cole et al. | .................. 250/341.8 |

FOREIGN PATENT DOCUMENTS

JP        EP 1271115 A2 *   1/2003    ............. G01N 21/21

OTHER PUBLICATIONS

Matsumoto et al., Measurement of the dielectric constant of thin films by terahertz time-domain spectroscopic ellipsometry, Jan. 15, 2011, Optics Letters, vol. 36, pp. 265-267.*
Barth et al., "Far-IR spectroscopic ellipsometer," Thin Solid Films 234, 314-317 (1993).
Bernhard et al., "Far-infrared ellipsometry using a synchrotron light source-the dielectric response of the cuprate high Tc superconductors," Thin Solid Films 455-456, 143-149 (2004).
Bilbro et al., "Temporal correlations of superconductivity above the transition temperature in La2-xSrxCuO4 probed by terahertz spectroscopy," Nat. Phys. 7, 298 (Feb. 2011).
Born and E. Wolf, Principles of Optics (Cambridge University Press, 1999), chap. 14, 7th ed.
Bremer et al., "Infrared ellipsometer for the study of surfaces, thin films, and superlattices," Appl. Opt. 31, 471-478 (1992).
Castro-Camus et al., "An ion-implanted InP receiver for polarization resolved terahertz spectroscopy," Opt. Express 15, 7047-7057 (2007).

(Continued)

*Primary Examiner* — Christine Sung
(74) *Attorney, Agent, or Firm* — Venable LLC; Henry J. Daley; Laura G. Remus (57) ABSTRACT

A terahertz time-domain spectroscopic ellipsometry system includes a sample stage, a terahertz emitter configured to provide pulses of terahertz radiation with preselected polarization components to illuminate a sample on the sample stage along an incident direction, and a coherent terahertz detection system arranged to coherently detect pulses of terahertz radiation from the terahertz emitter along an emerging direction after at least one of reflecting from or passing through the sample. The sample stage is rotatable to vary a relative angle between the incident direction and the emerging direction, and the coherent terahertz detection system substantially maintains alignment for amplitude and polarization detection as the relative angle is varied.

5 Claims, 9 Drawing Sheets

(56) References Cited

OTHER PUBLICATIONS

Dong et al., "Polarization state and mueller matrix measurements in terahertz-time domain spectroscopy," Optics Communications 282, 3671-3675 (2009).

Fischer et al., "Far-infrared vibrational modes of DNA components studied by terahertz time-domain spectroscopy," Physics in Medicine and Biology 47, 3807 (2002).

Gong et al., "Cross-polarization response of a two-contact photoconductive terahertz detector," Terahertz Science and Technology 4, 137-148 (Sep. 2011).

Grischkowsky et al., "Far-infrared time-domain spectroscopy with terahertz beams of dielectrics and semiconductors," J. Opt. Soc. Am. B 7, 2006-2015 (1990).

Hensley et al., "Extremely high coupling and transmission of high-powered-femtosecond pulses in hollow-core photonic band-gap fiber," in "Proceedings of Lasers and Electro-Optics," (San Jose, Calif., 2008), p. JFG1.

Hofmann et al., "Variable-wavelength frequency-domain terahertz ellipsometry," Rev. Sci. Instrum. 81, 023101 (2010).

Johs, "Regression calibration method for rotating element ellipsometers," Thin Solid Films 234, 395-398 (1993).

Kircher et al., "Far-infrared ellipsometry using synchrotron radiation," J. Opt. Soc. Am. B 14, 705-712 (1997).

Matsumoto et al., "Measurement of the dielectric constant of thin films by terahertz time-domain spectroscopic ellipsometry," Opt. Lett. 36, 265-267 (Jan. 2011).

Matsumoto et al., "Measurement of the soft-mode dispersion in SrTiO3 by terahertz time-domain spectroscopic ellipsometry," Japanese Journal of Applied Physics 48, 09KC11 (2009).

Mittleman et al., "Gas sensing using terahertz time-domain spectroscopy," Applied Physics B: Lasers and Optics 67, 379-390 (1998).

Morris et al., "Polarization modulation time-domain terahertz polarimetry," Opt. Express 20, 12303-12317 (May 2012).

Nagashima et al., "Measurement of complex optical constants of a highly doped Si wafer using terahertz ellipsometry," Applied Physics Letters 79, 3917-3919 (2001).

Nashima et al., "Measurement of optical properties of highly doped silicon by terahertz time domain reflection spectroscopy," Appl. Phys. Lett. 79, 3923 (2001).

Neshat et al., "Improved measurement of polarization state in terahertz polarization spectroscopy," Opt. Lett. 37, 1811-1813 (Jun. 2012).

Pashkin et al., "Phase-sensitive time-domain terahertz reflection spectroscopy," Rev. Sci. Instrum. 74, 4711 (2003).

Rubano et al., "Mid-infrared time-domain ellipsometry: Application to Nb-doped SrTiO3," Applied Physics Letters 101, 081103 (Aug. 2012).

Shimano et al., "Terahertz frequency Hall measurement by magneto-optical Kerr spectroscopy in InAs," Applied Physics Letters 81, 199-201 (2002).

Yasumatsu et al., "T-ray topography by time-domain polarimetry," Opt. Lett. 37, 2706-2708 (Jul. 2012).

* cited by examiner

TERAHERTZ TIME-DOMAIN SPECTROSCOPIC ELLIPSOMETRY SYSTEM

CROSS-REFERENCE OF RELATED APPLICATION

This invention was made with Government support of Grant No. YFA N66001-10-1-4017, awarded by the DARPA. The U.S. Government has certain rights in this invention.

BACKGROUND

1. Field of Invention

The field of the currently claimed embodiments of this invention relates to terahertz ellipsometry systems, and more particularly to terahertz time-domain spectroscopic ellipsometry systems.

2. Discussion of Related Art

Terahertz time-domain spectroscopy (THz-TDS) has tremendously grown with a wide range of applications [1]-[4]. It is now relatively routine to obtain complex (i.e. real and imaginary) spectral information, for instance the complex dielectric function, with absolute numerical values when performing measurements in a transmission geometry. However, transmission measurements are not possible on many materials and so far the technique has been difficult to apply to many metals, thick or highly doped semiconductors, coatings on thick substrates, substances in aqueous solution, and any otherwise opaque compound. Moreover, an outstanding technical problem with THz-TDS continues to be the determination of absolute spectral values when performing measurements in a reflection geometry [5]-[6]. A reason why THz time-domain reflection measurements are challenging is that the time-domain technique rests on the ability to detect the relative amplitude and phase of a time-dependent electric field of a sample as compared to a reference. In transmission measurements, transmission through an aperture is used as a reference. For reflection based THz time-domain a simple mirror cannot easily be used as a reference because its surface would need to be positioned within a fraction of a micron in exactly the same place as the sample so that the reflected positioning is challenging. Ellipsometry is a well-established technique in the optical range whereby the measurement of the two orthogonal polarization components of light reflected at glancing incidence allows a complete characterization of a sample's optical properties at a particular frequency [7]. Typically, one measures the two orthogonal polarization components by a complete 360° characterization of the waves amplitude using rotating polarizers. Importantly, ellipsometry obviates the need for measurement against a standard reference sample, and so can provide reliable spectroscopic information even when surface morphology is unknown, of marginal quality and/or a reference is unavailable. It is also self-referencing, so signal to noise ratios can be very good, as source fluctuations are divided out. In order to overcome the technical problems mentioned above for THz reflectivity, ellipsometry techniques have been recently revisited for terahertz range by using a backward wave oscillator source and a Golay cell power detector [8]. There have been a number of attempts to extend ellipsometry to far-infrared frequencies using conventional Fourier Transform Spectroscopy technology [9]-[13]. Unfortunately the lack of sufficiently intense sources (in addition to the calibration issues we confront here) has meant that such efforts have been challenging, although synchrotron-based efforts have made some important contributions in this regard [12]-[13]. Generally, these studies are limited to even higher frequencies (>4 THz) than we are here.

Combining ellipsometry with THz-TDS leads to a new technique called terahertz time-domain spectroscopic ellipsometry (THz-TDSE), in which a (sub)picosecond pulse with known polarization state is used as a probe to illuminate the sample, and then the modified polarization state by the sample is detected upon reflection or transmission. Unlike conventional optical ellipsometry, the reflected (transmitted) signal is detected coherently in the time-domain which allows one to obtain both amplitude and phase of the light in the two orthogonal directions. By transforming the time-domain data into the frequency domain through Fourier analysis, it is possible to extract ellipsometric parameter spectra similar to the standard optical spectroscopic ellipsometry. However, it should be noted that the instrumentation, signal analysis and calibration methods in THz-TDSE would differ from those in the standard optical ellipsometry, and all need to be revised accordingly. M. Hangyo and his coworkers, in their pioneering works, have demonstrated the potential of THz-TDSE for measuring the complex optical constants of a Si wafer with low resistivity, the soft-mode dispersion of SrTiO3 bulk single crystals and the dielectric constants of doped GaAs thin films [14]-[16]. There are very few other reports on using the THz-TDSE [17] technique, however, there are various reports on THz polarimetry [18]-[22] for material characterization. None of the proposed THz-TDSE experimental setups can provide an easy way of changing the angle of incidence without tedious work of optical/terahertz realignments. Moreover, less attention has been paid on the compensation of the non-idealities of the optical components and the alignments in THz-TDSE through a calibration scheme. Therefore, there remains a need for improved terahertz time-domain spectroscopic ellipsometry systems.

SUMMARY

A terahertz time-domain spectroscopic ellipsometry system according to some embodiments of the current invention includes a sample stage, a terahertz emitter configured to provide pulses of terahertz radiation with preselected polarization components to illuminate a sample on the sample stage along an incident direction, and a coherent terahertz detection system arranged to coherently detect pulses of terahertz radiation from the terahertz emitter along an emerging direction after at least one of reflecting from or passing through the sample. The sample stage is rotatable to vary a relative angle between the incident direction and the emerging direction, and the coherent terahertz detection system substantially maintains alignment for amplitude and polarization detection as the relative angle is varied.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention provide a new system for THz-TDSE in which the incidence angle in the reflection mode can change very easily in the range of 15°-85° with no need for any realignment. The same setup can be transformed into transmission mode with the same ease. Moreover, we provide a calibration scheme that can compensate for the non-ideality of the polarization response of the THz photoconductive antenna detector as well as that of wire grid polarizers used in the setup. In our calibration scheme, the ellipsometric parameters are obtained through a regression algorithm which we have adapted from the conventional regression calibration method developed for rotating element optical ellipsometers, and used here for the first time for THz-TDSE. As a demonstration, we present the characterization results for a high resistivity silicon substrate and a highly phosphorus doped Si substrate. Each sample was characterized with different angle of incidence.

Figure 1A:
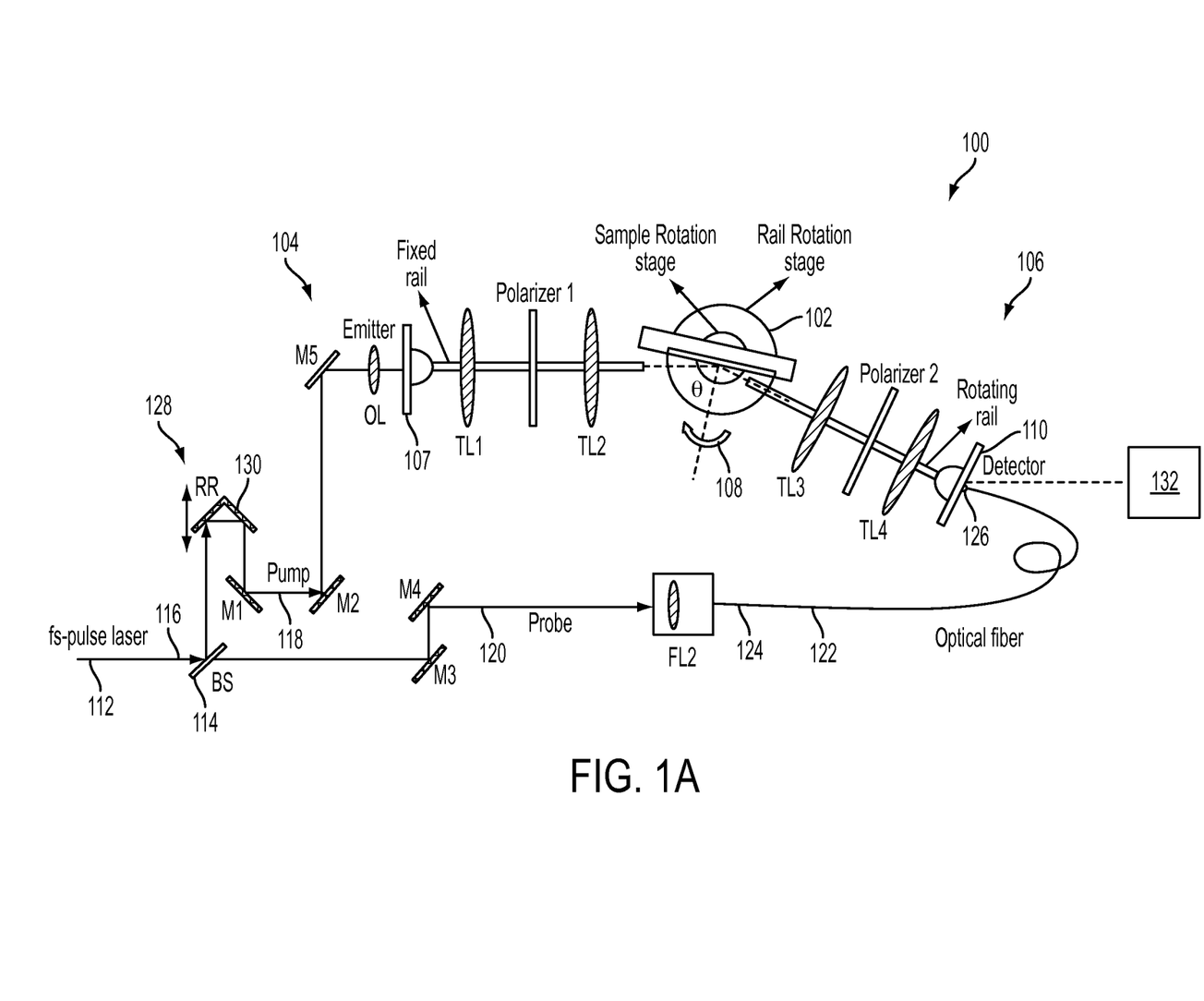
FIG. 1A is a schematic illustration of a terahertz time-domain spectroscopic ellipsometry system according to an embodiment of the current invention.
Figure 1B:
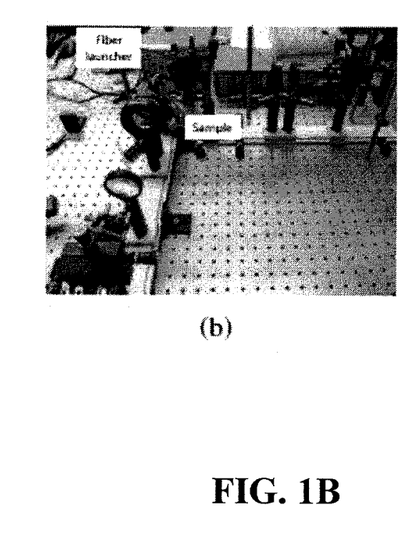
FIG. 1B shows a lab setup configured in reflection mode at 45° incidence angle for the embodiment of FIG. 1A.

FIG. 1 provides a schematic illustration of a terahertz time-domain spectroscopic ellipsometry system 100, according to an embodiment of the current invention. The terahertz time-domain spectroscopic ellipsometry system 100 includes a sample stage 102, a terahertz emitter 104 configured to provide pulses of terahertz radiation with preselected polarization components to illuminate a sample on the sample stage 102 along an incident direction, and a coherent terahertz detection system 106 arranged to coherently detect pulses of terahertz radiation from the terahertz emitter 107 along an emerging direction after at least one of reflecting from or passing through the sample. The sample stage 102 is rotatable to vary a relative angle 108 between the incident direction and the emerging direction. The coherent terahertz detection system 106 substantially maintains alignment for amplitude and polarization detection as the relative angle 108 is varied.

The coherent terahertz detection system 106 includes a terahertz detector 110. In some embodiments, the terahertz emitter 107 and the terahertz detector 110 are substantially identical photoconductive dipole antennas.

In some embodiments, the terahertz time-domain spectroscopic ellipsometry system 100 can further include a pulsed laser 112, and a beam splitter 114 arranged in an optical path 116 of light from the pulsed laser 112 to direct a pump beam of pulsed laser light 118 to the terahertz emitter 107 and a probe beam of pulsed laser light 120 to the terahertz detector 110. In some embodiments, the terahertz time-domain spectroscopic ellipsometry system 100 can further include an optical fiber 122 having an input end 124 fixed with respect to and optically coupled with the probe beam 120. The optical fiber 122 has an output end 126 that is fixed relative to the terahertz detector such that it remains substantially fixed as the relative angle 108 is varied to maintain alignment. In some embodiments, the optical fiber 122 can be a hollow core photonic band-gap fiber.

In some embodiments, the terahertz time-domain spectroscopic ellipsometry system 100 can further include a variable time-delay element 128 disposed in at least one of an optical path of the pump beam 118 or an optical path of the probe beam 120 so as to allow varying relative timing between illumination pulses and detected pulses. In some embodiments, the variable time-delay element 128 includes a slidable retroreflector 130 disposed in an optical path of the pump beam 118.

In some embodiments, the terahertz time-domain spectroscopic ellipsometry system 100 can further include a signal processing system 132 configured to communicate with the detection system 106 to receive detection signals. In some embodiments, the detection system provides time domain detection signals, and the signal processing system 132 is configured to perform a Fourier transform on the time domain detection signals to provide frequency domain data. The said signal processing system 132 can be further configured to process the frequency domain data to obtain absolute amplitude and polarization information for the sample. The said signal processing system 132 can be further configured to perform calibration corrections on the frequency domain data.

The following examples will describe some more details of some embodiments of the current invention. However, the broad concepts of the current invention are not limited only to these particular examples.

EXAMPLES

Figure 1C:
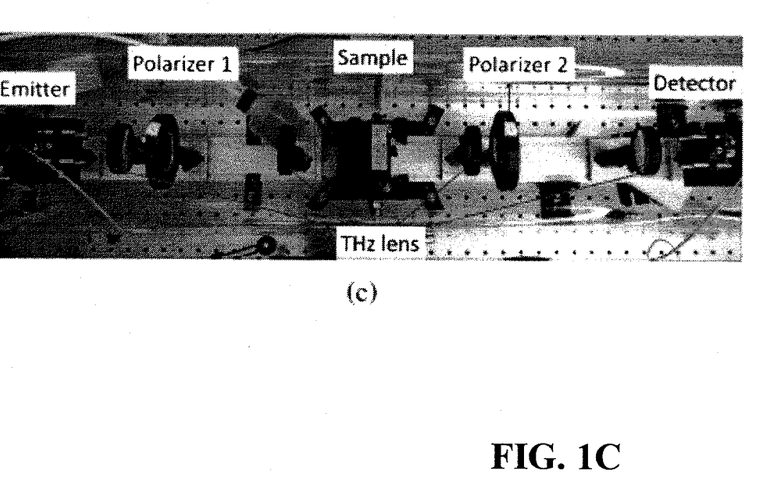
FIG. 1C shows a lab setup configured in transmission mode for the embodiment of FIG. 1A.

FIG. 1A illustrates an example of a terahertz time-domain spectroscopic ellipsometry system according to an embodiment of the current invention. In this system, the terahertz components are arranged on two straight arms using optical rails; one arm with THz emitter is fixed on the optical table, whereas the other arm with THz detector can rotate around a center point where the sample is placed. The sample sits on a second rotation stage. Such a configuration provides variable incidence angle (15°<θ<85°) in reflection mode, and can be easily configurable in transmission mode by aligning the arms along a straight line (FIG. 1C). In this schematic of the THz-TDSE setup with variable incidence angle in reflection mode that is also configurable in transmission mode optical components are labeled as follows, including a numerical value for each individual component (M, mirror; RR, retro-reflector; BS, optical beam splitter; OL, optical lens; TL, terahertz lens).

The setup uses an 8 f confocal geometry with terahertz lenses made of poly-4-methyl-pentacene-1 (TPX), which is a terahertz- and optically transparent material. Terahertz lenses have 50.8 mm clear aperture diameter and 100 mm focal length, and are less prone to misalignments and polarization distortion as compared to off-axis parabolic mirrors. The terahertz beam profile can be approximated as Gaussian. The sample is placed at the focal point of the terahertz lenses where an effective flat phase front exist at the beam waist. Based on the Gaussian beam assumption and 100 mm focal length for the THz lenses, the f# is approximately 9 for 0.2 THz. In the present case, the strong focusing and long wavelengths minimize the effects of a spread of incidence angles because an effective flat phase front exists at the sample position. This is the opposite approach than has been used in previous infrared ellipsometers that were designed to work at high f# [13]. Two identical photoconductive dipole antennas with collimating substrate lens are used as THz emitter and detector. Two rotatable polarizers are placed in the collimated beams immediately before the detector, and after the emitter as shown in FIG. 1. Polarizers were wire grid with wire diameter and spacing of 10 μm and 25 μm, respectively, and field extinction ratio of ~40:1 at 1 THz.

The laser source is an 800 nm Ti:sapphire femtosecond laser with pulse duration of <20 fs and 85 MHz repetition rate, which is divided into pump and probe beams. The pump beam is guided and focused onto the gap of the emitter photoconductive antenna through free-space optics in the usual fashion. However, the probe beam is guided toward the detector antenna on the rotating arm by a 1 m long hollow core photonic band-gap fiber (HC-PBGF). Using a fiber-coupled THz detector facilitates the rotation of the detector arm with no need for realignment of the optics for each incidence angle. The advantage of HC-PBGF is that it exhibits extremely low nonlinearity, high breakdown threshold, zero dispersion at the design wavelength, and negligible interface reflection [23]. Near zero dispersion of such fibers eliminates the need for optical pulse pre-chirping, which makes the optical setup and the alignments considerably simpler than using conventional fibers with pre-chirping.

Figure 2A:
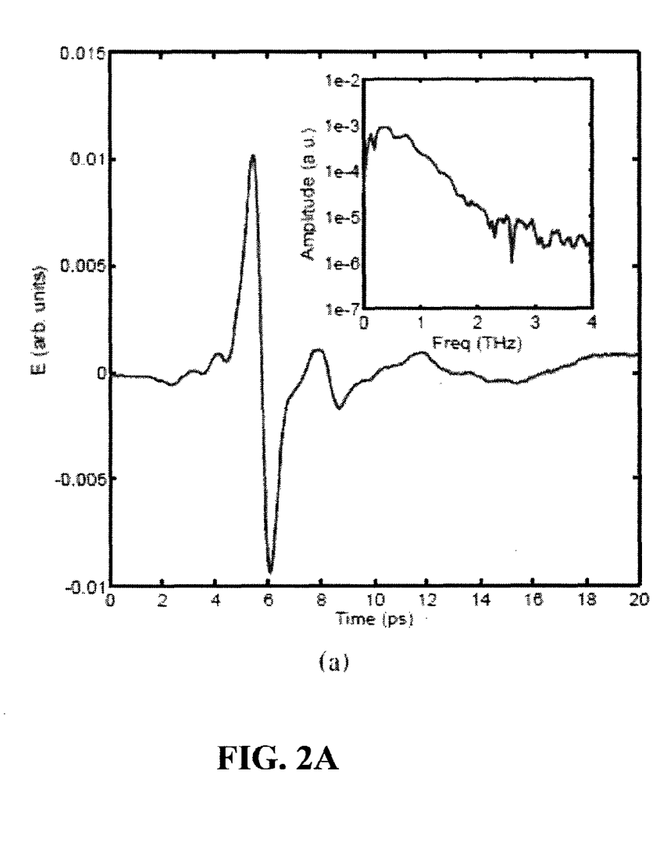
FIGS. 2A-2B show typical THz pulse detected in transmission mode when the probe beam is guided through (a) 1-m- long hollow core photonic band-gap fiber, (b) free-space optics. Insets show the corresponding pulse spectra.
Figure 2B:
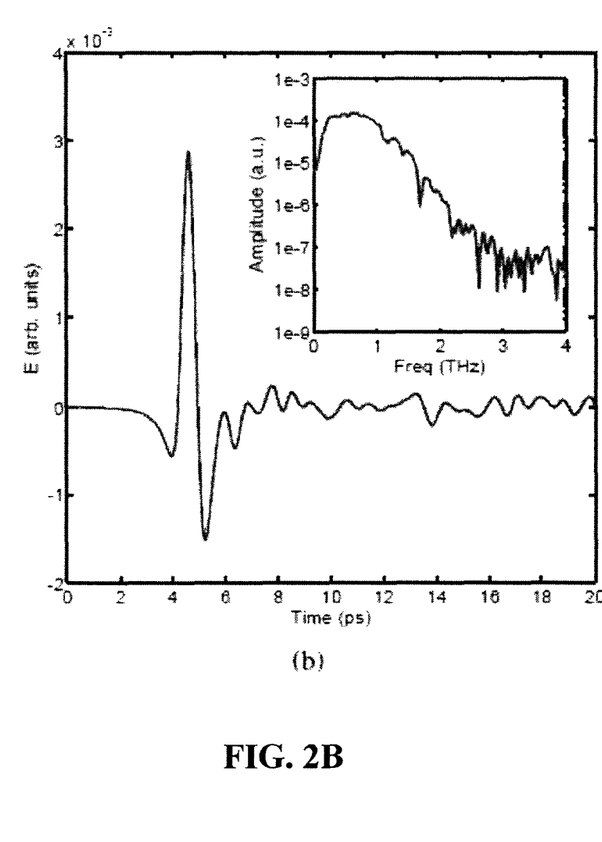
Figure 3A:
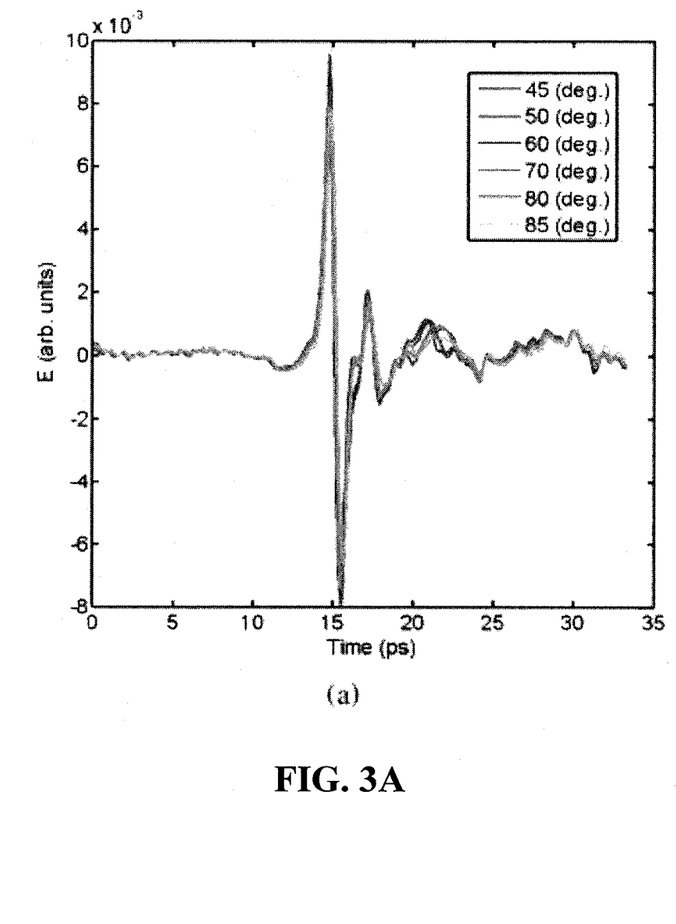
FIGS. 3A-3B show (a) Time-domain THz pulse and (b) its corresponding spectrum in reflection mode for various incidence angles. A silver mirror was used as the reflector.
Figure 3B:
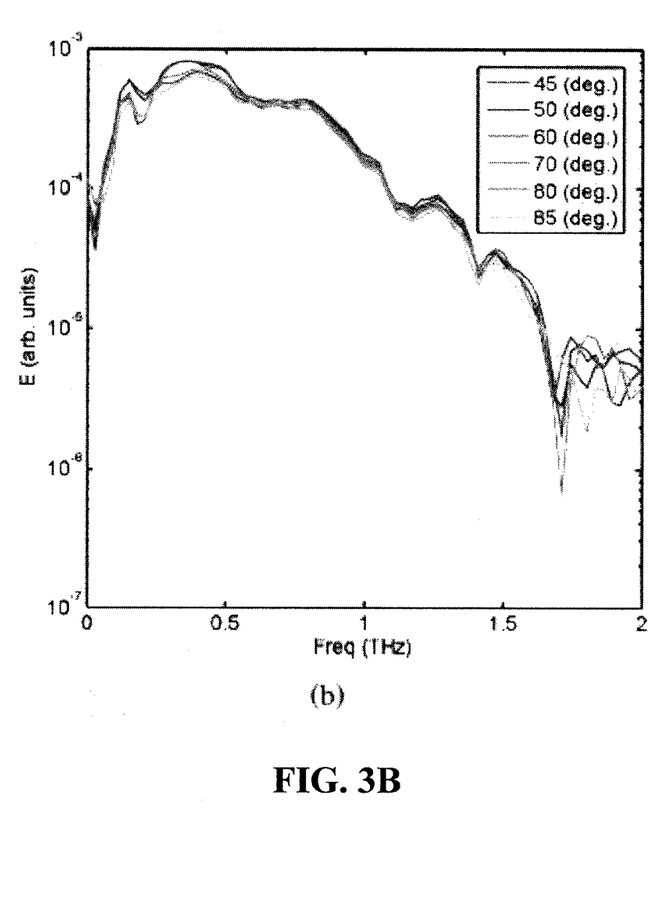

The fiber used in our setup is commercially available HC-800-2 from NKT Photonics. This fiber, fabricated by a stack-and-draw method, has a low-loss transmission band-gap of 100 nm centered around 820 nm. The core diameter is 7:5 μm, and the mode-field diameter is 5:5 μm. Attenuation through the low-loss region is reported as <250 dB/km. The fiber is connected from one side to a fiber launcher with a focusing lens and a 3-axis positioner, and from the other side is connected to a fiber-coupled focusing optics that is attached to the THz detector compartment. The temporal terahertz pulse is acquired by a lock-in amplifier during a time window within which the time delay between terahertz pulse and the sampling probe laser is swept by continuous movement of the retro-reflector. The pump beam is mechanically chopped, and the lock-in amplifier is synchronized to the chopping frequency. The acquired temporal signal is then taken into the frequency domain through a Fourier transform. FIG. 2 shows a typical THz pulse detected in transmission mode without any sample. In FIG. 2, one can compare the time-domain pulse shape and its spectrum detected when the probe beam is delivered to the detector by a 1 m long hollow core photonic band-gap fiber vs. free-space coupling. FIG. 3 shows the THz pulse and its corresponding spectrum in reflection using fiber coupling for various incidence angles without any optics realignment after changing the incidence angle. One can see that in this setup, any changes in the overall intensity at different angles are very small. In the reflection measurements a silver mirror was used as a reflector.

Formulation

Real-valued ellipsometric parameter spectra (Ψ;Δ) are obtained as a result of the spectroscopic ellipsometry measurement. These parameters are related to the complex ratio of the polarization eigenstates corresponding to the p and s components of the electric field vector (p- and s-axis are defined perpendicular to the propagation direction, and parallel and perpendicular to the incidence plane, respectively). Specifically, tan Ψ and Δ are defined as the absolute value and the phase of the complex ratio, respectively, when the incident polarization state is linear and at 45° azimuthal angle [7]. Once Ψ and Δ spectra are obtained from experiments, the optical constants and layer thicknesses can be generally extracted by fitting proper dielectric functions and optical models to the measured Ψ and Δ parameters. In a specific case of a bulk sample the complex refractive index (n–jk) can be obtained directly from the ellipsometric parameters using the expressions [24] where θ is the incidence angle, and tan Φ=1=tan Ψ.

Figure 4:
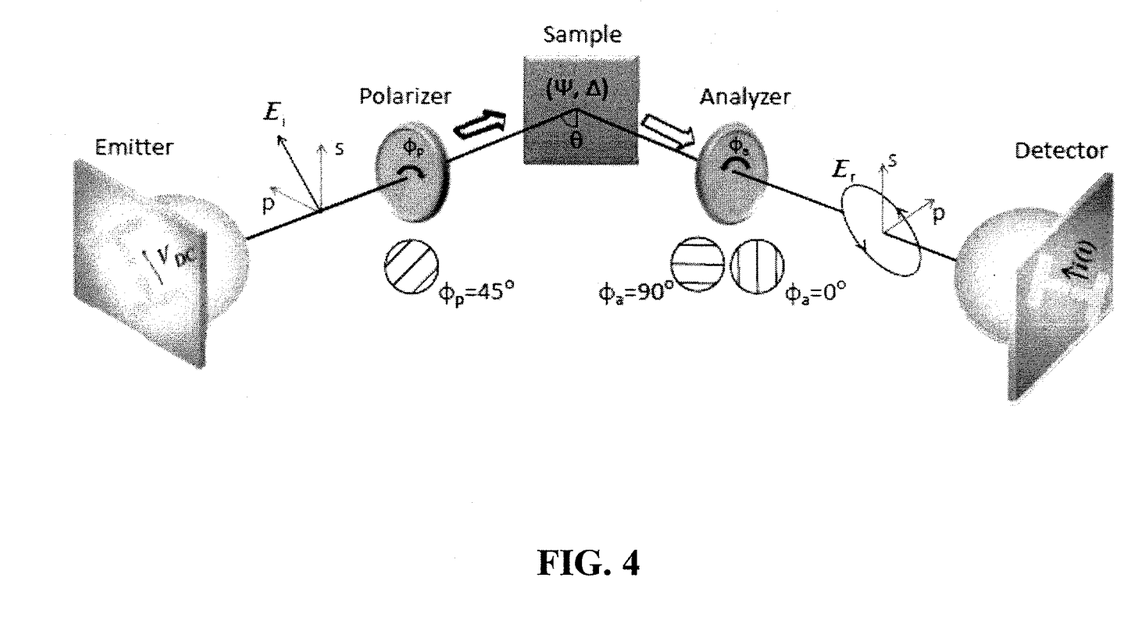
FIG. 4 is a schematic illustration of a terahertz time-domain spectroscopic ellipsometry system according to an embodiment of the current invention.

FIG. 4 illustrates a schematic of the optical configuration of the THz-TDSE in reflection mode. A biased photoconductive dipole antenna (Emitter) generates the incident field Ei=[Eip Eis] with close to linear polarization state and azimuthal angle around 45°. After passing through the polarizer, the polarization state becomes highly linear at the azimuthal angle of the polarizer φp. The reflected polarization state is then modified according to the ellipsometric parameters (Ψ;Δ) of the sample. The p- and s-component of the reflected polarization state are detected by setting the azimuthal angle of the analyzer at φa=0° and 90°, respectively.

In frequency domain, the Jones vector of the light beam at the THz detector, Er=[Erp Ers] as shown in FIG. 4, is determined by the product of the Jones matrices of the polarizer JP, sample JS, and analyzer JA as [7]

$$E_r = R(-\phi_a) J_A R(\phi_a) J_S R(-\phi_p) J_P R(\phi_p) E_i, \quad (2)$$

where R(φ) is the rotation matrix with angle φ. The Jones matrices for the sample and the polarizer/analyzer are given as [7]

$$J_s = \begin{bmatrix} \sin(\Psi)\exp(j\Delta) & 0 \\ 0 & \cos(\Psi) \end{bmatrix}, \quad (3)$$

$$J_{P(A)} = \begin{bmatrix} 1 & 0 \\ 0 & \eta_{P(A)}\exp(j\delta_{P(A)}) \end{bmatrix},$$

where ηP(A) is the extinction ratio of the polarizer (analyzer), defined as the ratio of the transmitted electric field when the polarizer transmission axis is perpendicular and parallel to the electric field direction, and δP(A) is the phase retardance. For an ideal polarizer/analyzer the extinction ratio is zero (ηP(A)=0).

In practice, the response of the THz detector is far from ideally linear polarization due to the non-ideality of the antenna geometry, and optical and terahertz alignments [25, 19]. Therefore, the polarization response of the THz detector should be taken into account by introducing a polarization state vector Pd=[Pp Ps], which is generally frequency dependent. In the frequency domain, the spectrum of the output signal of the photoconductive antenna detector can be expressed by an inner product as [26]

$$I = P_d(\omega) \cdot E_r, \quad (4)$$

where I is the Fourier transform (spectrum) of the THz detector output signal, Er is the electric field vector impinging on the detector as shown in FIG. 4, and ω is the angular frequency. We define a complex parameter ρ as the ratio of the detector output spectrum when the transmission axis of the analyzer is along p- and s-axis which corresponds to $\phi_a=0°$ and 90°, respectively, as $$\rho_{mod(exp)}(\Psi \cdot \Delta \cdot \phi_p \cdot \eta_{P(A)}, \delta_{P(A)}) = \frac{I_{mod(exp)}(\phi_a = 0°)}{I_{mod(exp)}(\phi_a = 90°)}. \quad (5)$$

where Imod and Iexp refer to the detector output spectrum calculated through the model described by Eqs. (2)-(4), and obtained directly from the experiment, respectively. From Eqs. (2)-(4), it is clear that the ρ-parameter is a function of the sample ellipsometric parameters (Ψ;Δ), azimuthal angle of the polarizer φp, and the extinction ratio and phase retardance of both polarizer and analyzer. It is worth noting that under ideal conditions, i.e. ηP(A)=0 and $P_d=[1/\sqrt{2}\ 1/\sqrt{2}]$, and for φp=45°, the ellipsometric parameters of the sample can be directly extracted from the ρ-parameter as $$\Psi = \tan^{-1}|\rho|, \Delta = \arg(\rho), \quad (6)$$

where arg(:) denotes the phase operator.

Measurement and Calibration Procedure

In order to accurately measure the ellipsometric parameters (Ψ;Δ) and consequently the optical constants through THz-TDSE, one needs to know the polarization state vector of the detector Pd, extinction ratio and phase retardance of the polarizer/analyzer as well as their azimuthal offset angles Δφp=Δφa with respect to the p-axis. Azimuthal offset angles may arise due to the uncertainty in the polarizer (analyzer), or the misalignment of the components (e.g. surface tilt of the sample), and can be easily modeled by replacing R(φp(a)) with R(φp(a)+Δφp(a)) in Eq. (2).

The complex vector Pd can be obtained experimentally over the desired frequency range through a calibration scheme reported elsewhere [26]. Using a gold mirror as the sample in FIG. 4, and by adapting the calibration scheme in [26] for the reflection mode, it is easy to show that $$P_d = \begin{bmatrix} P_p \\ P_s \end{bmatrix} = \begin{bmatrix} \sqrt{\frac{1+s}{2}} + \sqrt{\frac{1-s}{2}} \exp(j\delta_d) \\ -\sqrt{\frac{1+s}{2}} + \sqrt{\frac{1-s}{2}} \exp(j\delta_d) \end{bmatrix}, \quad (7)$$

where $$s = \frac{1 - |\kappa|^2}{1 + |\kappa|^2}. \quad (8)$$

$$\delta_d = \arg(\kappa), \quad (9)$$

$$\kappa = \frac{I_{exp}(\phi_a = 0°) - I_{exp}(\phi_a = 90°)}{I_{exp}(\phi_a = 0°) + I_{exp}(\phi_a = 90°)}. \quad (10)$$

Once Pd is known from Eq. (7) and through the reflection measurement from a gold mirror, the ellipsometric parameters are obtained through a regression algorithm which we have adapted from the conventional regression calibration method developed by B. Johs for rotating element optical ellipsometers [27], and used here for the first time for THz-TDSE. In our regression algorithm, the ρ-parameter defined in Eq. 5 is obtained experimentally (ρexp) from an isotropic sample at one or several different azimuthal angles of the polarizer (φpi; i=1; : : : ; N). Then, the ρ-parameter from the model (ρ mod) described by Eqs. (2)-(5) is fitted to that from the experiment over the desired frequency range and simultaneously for all the polarizer azimuthal angles, using the Levenberg-Marquardt nonlinear regression algorithm. We define an error function Err based on least squares fitting as $$Err = \sum_{\phi_{pi}} \sum_{\omega_j} [|\rho_{mod}(\omega_j, \phi_{pi}, \Psi, \Delta, \ldots)| - |\rho_{exp}(\omega_j, \phi_{pi})|]^2 + \quad (11)$$

$$[\arg(\rho_{mod}(\omega_j, \phi_{pi}, \Psi, \Delta, \ldots)) - \arg(\rho_{exp}(\omega_j, \phi_{pi}))]^2.$$

It should be noted that all measurements and computations in this section are made in discrete time and frequency domains. In the regression algorithm, the ellipsometric parameters Ψ and Δ, as well as the polarizer/analyzer parameters ηP(A), δP(A) and Δφp(a) are simultaneously found such that the error function defined in Eq. (11) is minimized over the measurement frequency range (ωj; j=1; : : : ; M) and for all measured data sets corresponding to different polarizer angles (φpi; i=1; : : : ; N). The advantage of this technique is that the polarizer/analyzer parameters do not need to be a priori knowledge, although reasonable initial values are necessary for the convergence of the regression algorithm. It was found that the best initial values for Ψ and Δ are those obtained from Eq. (6) when ρ=ρ exp.

Experimental Results and Discussion

As a demonstration, two different silicon samples were tested. The first sample was a 0.4-mm-thick high resistivity Si substrate with polished surface. For this sample the reflected time-domain pulse was truncated right before the arrival of the second reflection in order to avoid Fabry-perot interferences due to the reflection from the back surface. The second sample was a 1-mm-thick highly phosphorus-doped Si substrate with nominal room temperature DC resistivity of 0:0151 Ω-cm.

Figure 5A:
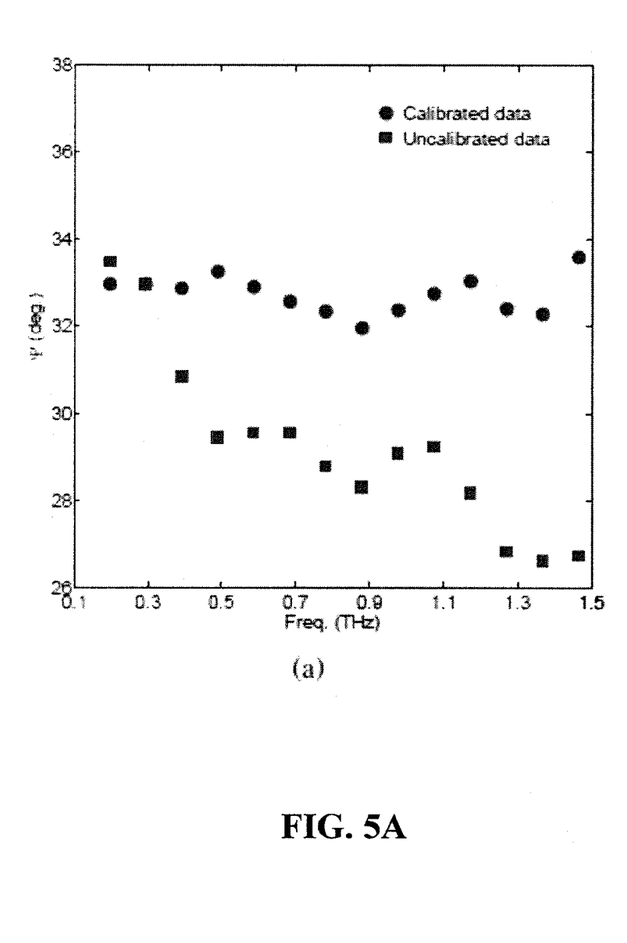
FIGS. 5A-5B show measured ellipsometric parameters (a) Ψ and (b) Δ for the high resistivity silicon substrate. Square and circle marks present the ellipsometric parameters before and after calibrating out the effect of the THz detector and the polarizer/analyzer, respectively. The incidence angle was 45°.
Figure 5B:
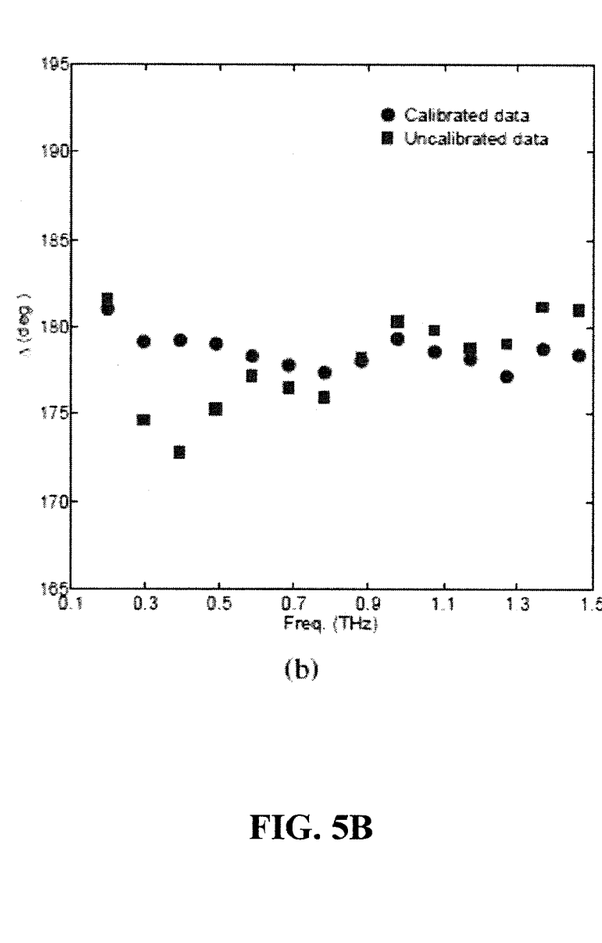

FIG. 5 shows the measured calibrated and uncalibrated ellipsometric parameters Ψ and Δ for the high-resistivity sample. The calibrated plots are obtained by fitting the ρ-parameter to three sets of measured data corresponding to polarizer angles φp1=25°, φp2=45° and φp3=65°. The uncalibrated plot is directly obtained from Eq. (6) using the data set corresponding to φp2=45°. An incidence angle of 45° (away from the Brewster's angle) was used for this experiment so as to have appreciable signal in both the s- and p-polarizations.

Figure 6:
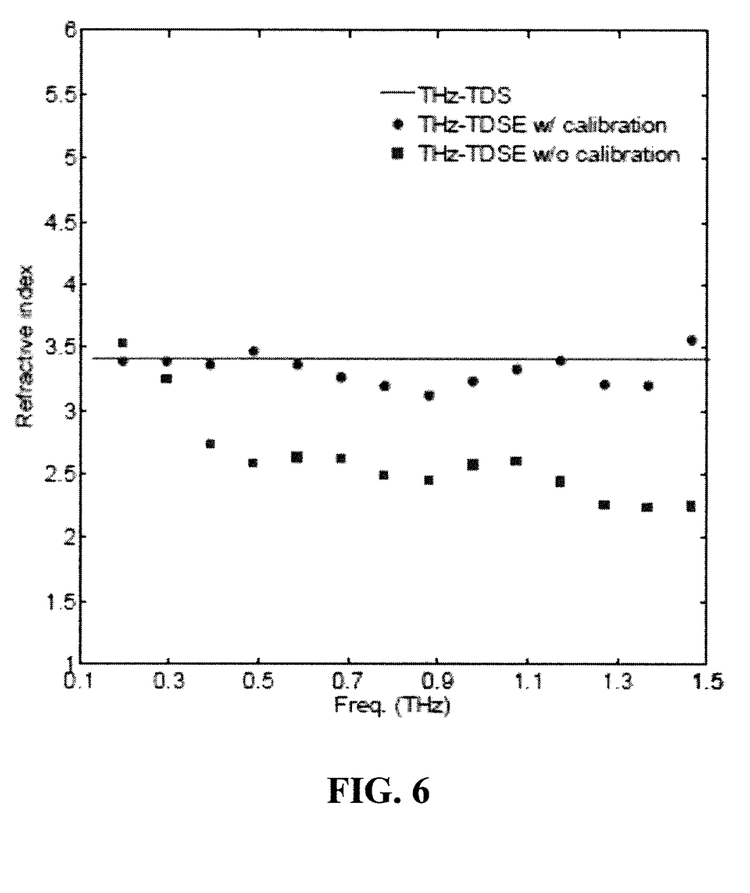
FIG. 6 shows extracted refractive index of the high resistivity silicon substrate from the uncalibrated (square) and calibrated (circle) ellipsometric parameters. Solid line shows the data from the conventional transmission THz-TDS reported in [1].

FIG. 6 compares the extracted refractive index, using Eq. (1), from the uncalibrated and calibrated ellipsometric parameters shown in FIG. 5 with that from the conventional transmission THz-TDS reported in [1]. It is evident that the calibration has substantially improved the measurement accuracy over the uncalibrated data. The ellipsometric measurements do not have as much precision as the transmission experiments. But this illustrates the important point that the power of ellipsometric measurements rests not on measuring dielectric properties of samples that could be measured in transmission, but in measuring samples that are otherwise opaque.

Figure 7A:
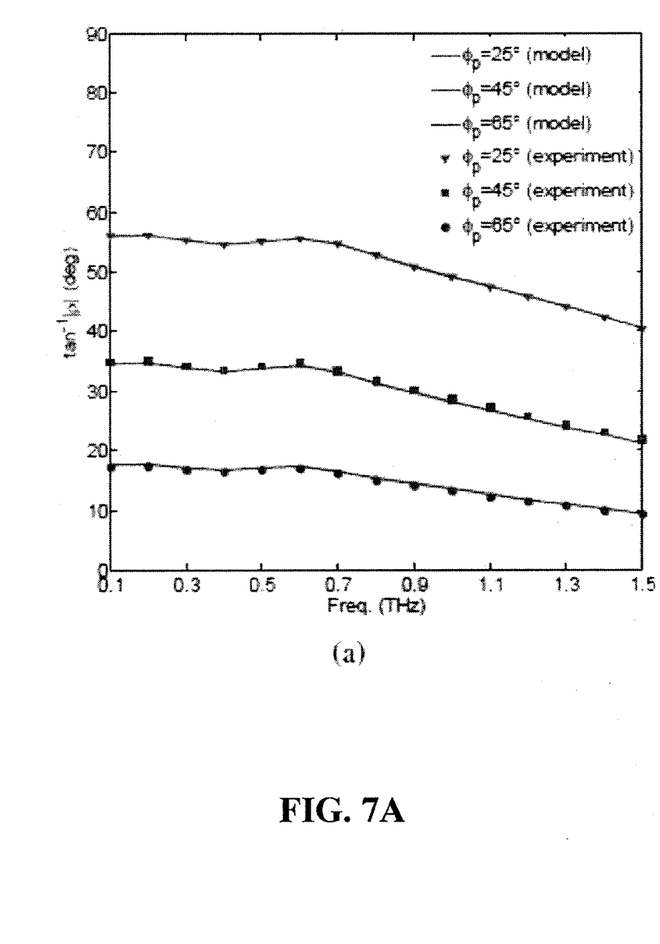
FIGS. 7A-7B are fitting results of the (a) amplitude and (b) phase of the ρ-parameter shown as solid lines for ρ mod and discrete marks for ρexp. The fitting was performed simultaneously for three sets of data corresponding to three different azimuthal angle of the polarizer and over the displayed frequency range. The sample was a highly doped silicon substrate, and the incidence angle was 73°.
Figure 7B:
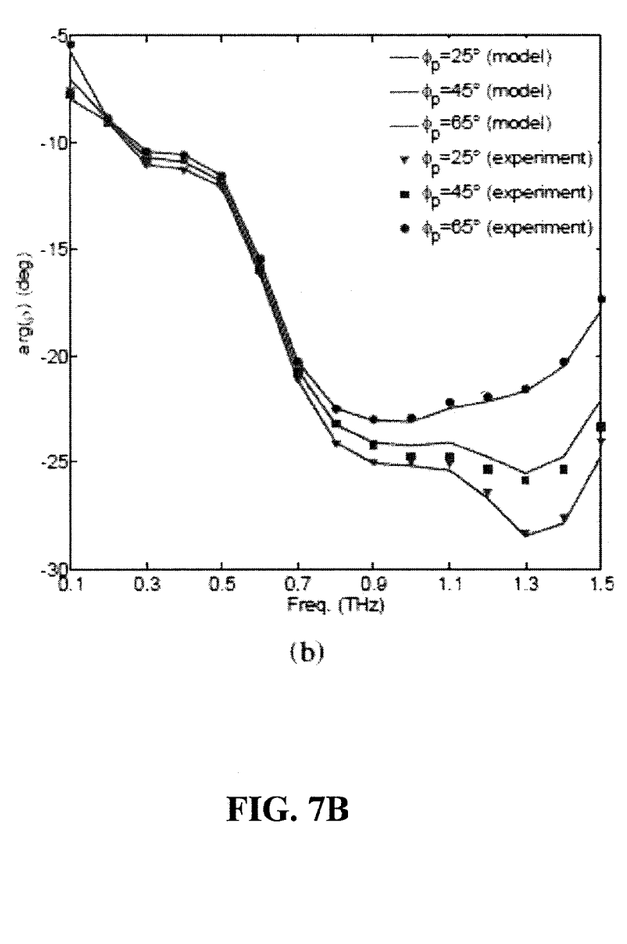

FIG. 7 shows the simultaneous fitting results of the amplitude and phase of the $\rho$ mod to $\rho\exp$ for the highly doped silicon sample over the frequency range 0.1-1.5 THz. The fitting was performed simultaneously for three sets of data corresponding to three different azimuthal angle of the polarizer. Ellipsometric parameters $\Psi$ and $\Delta$ along with polarizer/analyzer extinction ratios, phase retardances and offset angles were the free parameters of the regression algorithm in this least squares fitting. This highly doped silicon sample is opaque in the THz range and cannot be measured in transmission. The incidence angle was 73°, which is close to the Brewster angle of silicon.

Figure 8A:
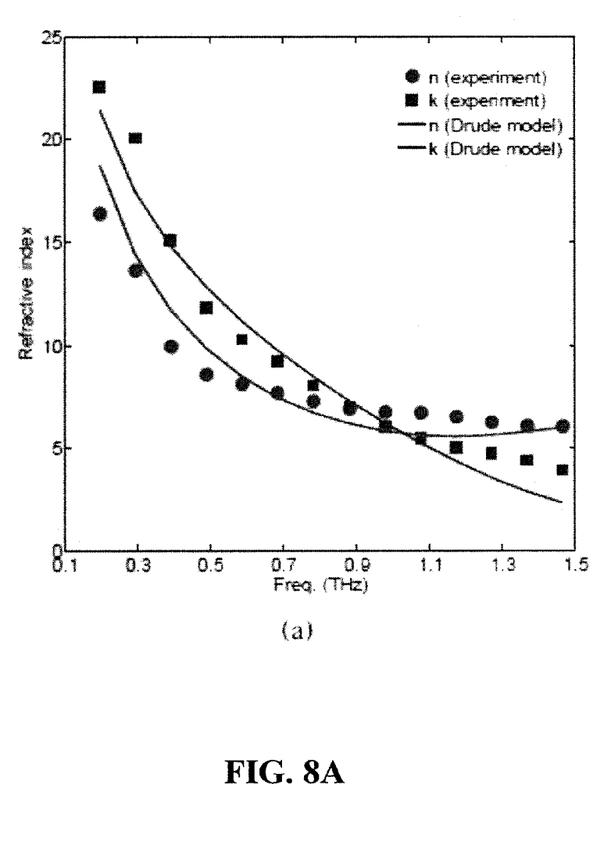
FIGS. 8A-8B shows (a) Extracted complex refractive index of the highly doped silicon substrate from ellipsometric parameters. Solid lines show the Drude model fit to the measured data. (b) Extracted resistivity of the highly doped silicon substrate from ellipsometry measurement. Square mark presents its DC resistivity measured via a non-contact eddy-current resistivity gauge (COTS ADE 6035).
Figure 8B:
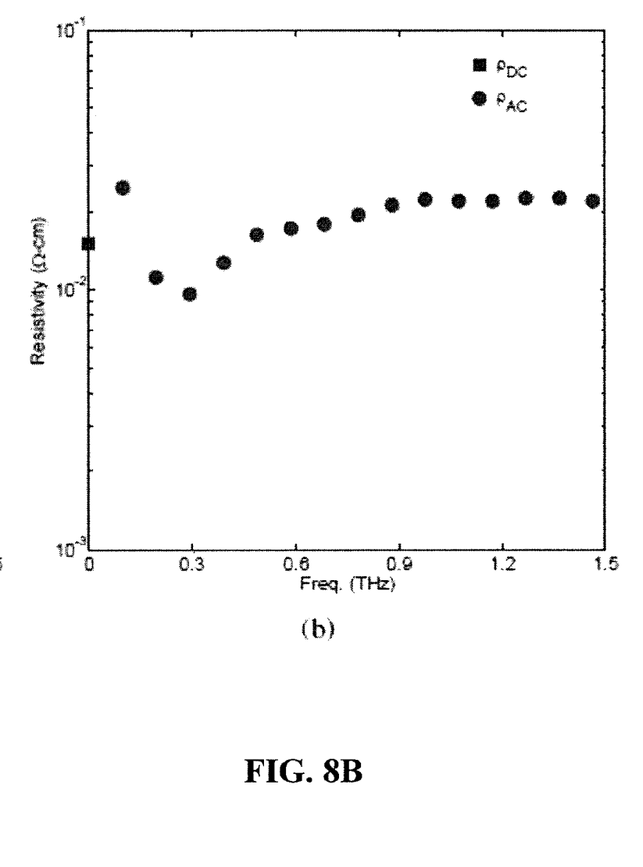

FIG. 8A shows the extracted complex refractive index of the highly doped silicon substrate from ellipsometric parameters (not shown) along with a Drude model fit to the measured data. FIG. 8B shows the AC resistivity of the highly doped silicon substrate extracted from the ellipsometry measurement. As shown, the measured AC resistivity is consistent with the DC resistivity measured via a non-contact eddy-current resistivity gauge (COTS ADE 6035).

In order to avoid water vapor absorption, the space with terahertz wave propagation was enclosed and purged with dry air during the above measurements.

CONCLUSION

Terahertz time-domain spectroscopic ellipsometry is a newly established characterization technique that collectively possesses the advantages of the well-established techniques of ellipsometry and THz-TDS. In this section, a new experimental setup for THz-TDSE was described that easily provides variable angle of incidence in the range of 15°-85° in the reflection mode. The setup can also be configured into transmission mode with the same ease. We used hollow core photonic band gap fiber without pre-chirping to deliver femtosecond laser to the THz photoconductive antenna detector that facilitates the change of the incidence angle. An effective calibration scheme was also described and applied for characterization of two different Si substrate samples as an initial demonstration.

REFERENCES AND LINKS

1. D. Grischkowsky, S. Keiding, M. van Exter, and C. Fattinger, "Far-infrared time-domain spectroscopy with terahertz beams of dielectrics and semiconductors," J. Opt. Soc. Am. B 7, 2006-2015 (1990).
2. B. M. Fischer, M. Walther, and P. U. Jepsen, "Far-infrared vibrational modes of DNA components studied by terahertz time-domain spectroscopy," Physics in Medicine and Biology 47, 3807 (2002).
3. D. Mittleman, R. Jacobsen, R. Neelamani, R. Baraniuk, and M. Nuss, "Gas sensing using terahertz time-domain spectroscopy," Applied Physics B: Lasers and Optics 67, 379-390 (1998).
4. L. Bilbro, R. V. Aguilar, G. Logvenov, O. Pelleg, I. Bozovic, and N. P. Armitage, "Temporal correlations of superconductivity above the transition temperature in La2-xSrxCuO4 probed by terahertz spectroscopy," Nat. Phys. 7, 298 (2011).
5. S. Nashima, O. Morikawa, K. Takata, and M. Hangyo, "Measurement of optical properties of highly doped silicon by terahertz time domain reflection spectroscopy," Appl. Phys. Lett. 79, 3923 (2001).
6. A. Pashkin, M. Kempa, H. Nemec, F. Kadlec, and P. Kuzel, "Phase-sensitive time-domain terahertz reflection spectroscopy," Rev. Sci. Instrum. 74, 4711 (2003).
7. H. Fujiwara, Spectroscopic Ellipsometry: Principles and Applications (John Wiley & Sons, 2007).
8. T. Hofmann, C. M. Herzinger, A. Boosalis, T. E. Tiwald, J. A. Woollam, and M. Schubert, "Variable-wavelength frequency-domain terahertz ellipsometry," Rev. Sci. Instrum. 81, 023101 (2010).
9. A. Roseler, Infrared Spectroscopic Ellipsometry (Akademie-Verlag, Berlin, 1990).
10. K.-L. Barth, D. Bhme, K. Kamars, F. Keilmann, and M. Cardona, "Far-IR spectroscopic ellipsometer," Thin Solid Films 234, 314-317 (1993).
11. J. Bremer, O. Hunderi, K. Fanping, T. Skauli, and E. Wold, "Infrared ellipsometer for the study of surfaces, thin films, and superlattices," Appl. Opt. 31, 471-478 (1992).
12. C. Bernhard, J. Humlcek, and B. Keimer, "Far-infrared ellipsometry using a synchrotron light source—the dielectric response of the cuprate high Tc superconductors," Thin Solid Films 455-456, 143-149 (2004).
13. J. Kircher, R. Henn, M. Cardona, P. L. Richards, and G. P. Williams, "Far-infrared ellipsometry using synchrotron radiation," J. Opt. Soc. Am. B 14, 705-712 (1997).
14. T. Nagashima and M. Hangyo, "Measurement of complex optical constants of a highly doped Si wafer using terahertz ellipsometry," Applied Physics Letters 79, 3917-3919 (2001).
15. N. Matsumoto, T. Fujii, K. Kageyama, H. Takagi, T. Nagashima, and M. Hangyo, "Measurement of the soft-mode dispersion in SrTiO3 by terahertz time-domain spectroscopic ellipsometry," Japanese Journal of Applied Physics 48, 09KC11 (2009).
16. N. Matsumoto, T. Hosokura, T. Nagashima, and M. Hangyo, "Measurement of the dielectric constant of thin films by terahertz time-domain spectroscopic ellipsometry," Opt. Lett. 36, 265-267 (2011).
17. A. Rubano, L. Braun, M. Wolf, and T. Kampfrath, "Mid-infrared time-domain ellipsometry: Application to Nb-doped SrTiO3," Applied Physics Letters 101, 081103 (2012).
18. R. Shimano, Y. Ino, Y. P. Svirko, and M. Kuwata-Gonokami, "Terahertz frequency Hall measurement by magneto-optical Kerr spectroscopy in InAs," Applied Physics Letters 81, 199-201 (2002).
19. E. Castro-Camus, J. Lloyd-Hughes, L. Fu, H. H. Tan, C. Jagadish, and M. B. Johnston, "An ion-implanted InP receiver for polarization resolved terahertz spectroscopy," Opt. Express 15, 7047-7057 (2007).
20. H. Dong, Y. Gong, V. Paulose, and M. Hong, "Polarization state and mueller matrix measurements in terahertz-time domain spectroscopy," Optics Communications 282, 3671-3675 (2009).
21. C. M. Morris, R. V. Aguilar, A. V. Stier, and N. P. Armitage, "Polarization modulation time-domain terahertz polarimetry," Opt. Express 20, 12303-12317 (2012).
22. N. Yasumatsu and S. Watanabe, "T-ray topography by time-domain polarimetry," Opt. Lett. 37, 2706-2708 (2012).
23. C. J. Hensley, M. A. Foster, B. Shim, and A. L. Gaeta, "Extremely high coupling and transmission of high-powered-femtosecond pulses in hollow-core photonic band-gap fiber," in "Proceedings of Lasers and Electro-Optics," (San Jose, Calif., 2008), p. JFG1.
24. M. Born and E. Wolf, Principles of Optics (Cambridge University Press, 1999), chap. 14, 7th ed.
25. Y. Gong, H. Dong and Z. Chen, "Cross-polarization response of a two-contact photoconductive terahertz detector," Terahertz Science and Technology 4, 137-148 (2011).
26. M. Neshat and N. P. Armitage, "Improved measurement of polarization state in terahertz polarization spectroscopy," Opt. Lett. 37, 1811-1813 (2012).
27. B. Johs, "Regression calibration method for rotating element ellipsometers," Thin Solid Films 234, 395-398 (1993).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A terahertz time-domain spectroscopic ellipsometry system comprising:
a sample stage;
a terahertz emitter configured to provide pulses of terahertz radiation with preselected polarization components to illuminate a sample on said sample stage along an incident direction;
a coherent terahertz detection system arranged to coherently detect pulses of terahertz radiation from said terahertz emitter along an emerging direction after at least one of reflecting from or passing through said sample, wherein said coherent terahertz detection system comprises a terahertz detector;
a pulsed laser;
a beam splitter arranged in an optical path of light from said pulsed laser to direct a pump beam of pulsed laser light to said terahertz emitter and a probe beam of pulsed laser light to said terahertz detector;
an optical fiber having an input end fixed with respect to and optically coupled with said probe beam;
a variable time-delay element disposed in at least one of an optical path of said pump beam or an optical path of said probe beam so as to allow varying relative timing between illumination pulses and detected pulses; and
a signal processing system configured to communicate with said detection system to receive detection signals,
wherein said sample stage is rotatable to vary a relative angle between said incident direction and said emerging direction,
wherein said coherent terahertz detection system substantially maintains alignment for amplitude and polarization detection as said relative angle is varied,
wherein said optical fiber has an output end that is fixed relative to said terahertz detector such that it remains substantially fixed as said relative angle is varied to maintain alignment,
wherein said detection system provides time domain detection signals,
wherein said signal processing system is configured to perform a Fourier transform on said time domain detection signals to provide frequency domain data, and
wherein said signal processing system is further configured to process said frequency domain data to obtain absolute amplitude and polarization information for said sample.

2. A terahertz time-domain spectroscopic ellipsometry system according to claim 1, wherein said signal processing system is further configured to perform calibration corrections on said frequency domain data.

3. A terahertz time-domain spectroscopic ellipsometry system according to claim 1, wherein said terahertz emitter and said terahertz detector are substantially identical photoconductive dipole antennas.

4. A terahertz time-domain spectroscopic ellipsometry system according to claim 1, wherein said variable time-delay element comprises a slidable retroreflector disposed in an optical path of said pump beam.

5. A terahertz time-domain spectroscopic ellipsometry system according to claim 1, wherein said optical fiber is a hollow core photonic band-gap fiber.

* * * * *